United States Patent [19]

Oshio et al.

[11] 4,244,731
[45] Jan. 13, 1981

[54] METHOD FOR CONTROLLING THE GROWTH OF PLANTS

[75] Inventors: Hiromichi Oshio, Minoo; Hiroyuki Konishi, Ibaraki; Shunji Matsumura, Hirakata; Kikuichi Ishikawa; Eiichi Yoneyama, both of Niihama, all of Japan

[73] Assignee: Sumitomo Chemical Company, Limited, Osaka, Japan

[21] Appl. No.: 896,487

[22] Filed: Apr. 14, 1978

[30] Foreign Application Priority Data

Apr. 18, 1977 [JP] Japan .................................. 52/44676

[51] Int. Cl.³ .................... A01N 37/34; A01N 37/38
[52] U.S. Cl. .......................................... 71/105; 71/76; 71/106; 71/109; 71/116
[58] Field of Search ................ 71/105, 109, 116, 106, 71/76

[56] References Cited

U.S. PATENT DOCUMENTS

| 2,790,819 | 4/1957 | Godfrey | 71/105 X |
| 2,823,225 | 2/1958 | Senkbeil et al. | 71/106 X |
| 3,338,703 | 8/1967 | Weil et al. | 71/106 |

FOREIGN PATENT DOCUMENTS 1450005  9/1976  United Kingdom .

OTHER PUBLICATIONS

Swiss Pat. 401,022, Chem. Abst. vol. 65, 8820g.
Chem Abst. vol. 68, 77968h, Russian Pat. 197,561.
Japanese Patent 88627–Derwent, Central Patent Index, 71172x138, (1976).
German Offen. 2,250,327, Chem. Abst. vol. 79, (1973), 53029d.
German Offen. 2,541,237, Chem. Abst. vol. 85, (42267c), 1976.
U.S. Patent 2,390,941, Chem. Abst. vol. 40, (1946), 2264⁵.
Morris, Chem. Abst. vol. 70, (1969), 86493t.

*Primary Examiner*—Catherine L. Mills
*Attorney, Agent, or Firm*—Stevens, Davis, Miller & Mosher

[57] ABSTRACT

A method for controlling the growth of plants, by applying to said plants a 2,6-dimethylphenoxy compound of the formula:

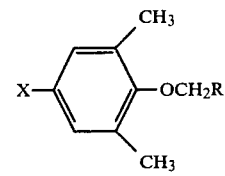

wherein R is hydroxycarbonyl, $C_{1-4}$ alkoxycarbonyl $C_{1-6}$ alkylcarboxymethyl, mono-, di- or tri-halo $C_{1-4}$ alkylcarboxymethyl or nitrile;

X is hydrogen or $C_{1-4}$ alkylcarbonyl, when R is $C_{1-6}$ alkylcarboxymethyl, mono-, di- or tri-halo $C_{1-4}$ alkylcarboxymethyl or nitrile; and X is $C_{1-4}$ alkylcarbonyl or benzoyl, when R is hydroxycarbonyl or $C_{1-4}$ alkoxycarbonyl.

12 Claims, No Drawings

METHOD FOR CONTROLLING THE GROWTH OF PLANTS

This invention relates to a method for regulating the growth of plants by applying to said plant a plants growth regulator which comprises as an active ingredient a 2,6-dimethylphenoxy compound of the formula:

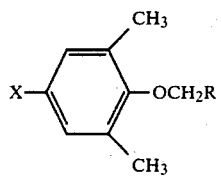

wherein R is hydroxycarbonyl, $C_{1-4}$ alkoxycarbonyl $C_{1-6}$ alkylcarboxymethyl, mono-, di- or tri-halo $C_{1-4}$ alkylcarboxymethyl or nitrile;
X is hydrogen or $C_{1-4}$ alkylcarbonyl, when R is $C_{1-6}$ alkylcarboxymethyl, mono-, di- or tri-halo $C_{1-4}$ alkylcarboxymethyl or nitrile; and
X is $C_{1-4}$ alkylcarbonyl or benzoyl, when R is hydroxycarbonyl or $C_{1-4}$ alkoxycarbonyl.

In the cultivation of plants, methods of better regulating the growth of plants so that they grow in a manner suitable for their particular use have, for a long period of time, depended upon finding an improvement in the variety of particular plants or on improving the technique of fertilization. As the mechanism of growth control of plants using plant hormones has become more well-known in recent years, positive attempts at obtaining direct plant growth regulating using chemical substances have been carried out. As a result, more and more chemicals are not utilized in agriculture and horticulture for this purpose, e.g., α-naphthaleneacetic acid for encouraging plant's cuttings to take root, gibberellin for making grapes seedless, and N,N-dimethylaminosuccinamic acid for the dwarfing of chrysanthemums. However, the number of uses to which plant growth regulators have been put is, in practice, far less than the total number for which successful application of regulators might be expected. Further, many problems have to be overcome before even those chemical substances which have already been developed can be applied in practice. For example, such compounds may vary in their effectiveness or cause phytotoxicity depending on the concentration in which and the time at which they are applied. Moreover, conventional plant growth regulators vary in their effectiveness, in general, depending on the kind of plant to be treated, and it is frequently found that substances which have effects on broad-leaved crops are entirely ineffective on rice crops, or substances which have effects on wheat have no effect on rice.

In an attempt to find a substance with which the growth of a wide variety of plants could be regulated we conducted extensive studies which revealed that 2,6-dimethylphenoxy compounds (I), previously defined, have prominent plant growth-regulating effects.

Hitherto, it is well known that halogen-substituted phenoxy derivatives as represented by 2,4-D are used as a herbicide or plant hormone agent. According to Japanese Pat. Appln. Kokai (Laid-Open) No. 88627/1976, 3,4-dichlorophenoxyacetic acid is claimed as a plant growth regulator. Further, as the methyl-substituted products of phenoxy derivatives, 2-methylphenoxypropionic acid is claimed as a herbicide in German Offenlegungsschrift No. 2,541,237; and substituted 2,6-dimethylphenoxyacetic acid derivatives (referred to as "DMPA" hereinafter) are said to have a plant growth regulating effect in German Offenlegungsschrift No. 2,407,148 and British Pat. No. 1,450,005; and acetyldialkylphenoxyacetic acid derivatives are said to have a pharmaceutical effect in German Offenlegungsschrift No. 2,250,327.

Still further, 2-alkylphenoxyethyl carboxylates are claimed as a plasticizer in Soviet Patent No. 197,561; and substituted phenoxyethyl carboxylates are claimed as a dyeing assistant in Swiss Patent No. 401,022.

In these patents, however, there is no description that these compounds have a plant growth regulating effect. This effect of 2,6-dimethylphenoxy compound (I) is a quite novel knowledge found by the inventor's original study. In the past, N,N-dimethylamino-succinamic acid (referred to as "B-9" hereinafter) above mentioned, has chiefly been used as a plant growth regulator for Potmum cultivation. However, it is well known that although when sprayed onto the stems and leaves of plants, N,N-dimethylamino-succinamic acid is effective, it is, when used in soil treatment, too weak in effectiveness to be useful in practice. In contrast, the 2,6-dimethylphenoxy compounds (I) show prominent growth-retarding activities both in foliar spray treatment and in soil drench treatment, and hence may be said to be extremely useful plant growth regulators. When the compounds in German Offenlegungsschrift No. 2,407,148 are applied to chrysanthemum, they display an effect to regulate the height of the plant, but at the same time, they display a remarkable phytotoxicity which lowers their commercial value to a large extent, while the 2,6-dimethylphenoxy compound (I) displays a constant effect over a wide range of concentration with no phytotoxicity. Consequently, the 2,6-dimethylphenoxy compound (I) is a plant growth regulator which is superior to the well-known ones in the practical value.

The 2,6-dimethylphenoxy compound (I) has effects not only to regulate the heights of ornamental plants (e.g., chrysanthemum, hibiscus and poinsettia) and cereals (e.g., wheat and barley) for increase of commercial value, but also to inhibit the growth to an undesirable length of succulent shoots of fruit trees (e.g., apple trees, grapevine, pear trees and orange) and turf, and to regulate the vegetative growth of fruit trees and so to properly regulate the flowering stage and fruit-ripening stage of the trees.

Thus the 2,6-dimethylphenoxy compound (I) can be used in various purposes.

Typical examples of compounds of the formula (I) and the physical properties thereof are shown in Table 1 hereinafter.

A main object of the present invention is to provide a method for regulating the growth of plants by appling to the plants a 2,6-dimethylphenoxy compound (I), which is useful as plant growth regulator, especially plant growth retardant.

Another object of this invention is to provide the plant growth regulating composition containing as an active ingredient a 2,6-dimethylphenoxy compound (I).

The 2,6-dimethylphenoxy compound (I) of the present invention may be produced in a high yield by the following conventional methods.

Procedure A

The 2,6-dimethylphenoxy compound of the formula,

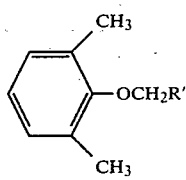
(II)

wherein R' is $C_{1-6}$ alkylcarboxylmethyl or mono-, di- or tri-halo $C_{1-4}$ alkylcarboxylmethyl group and can be prepared by reacting a 2,6-dimethylphenoxyethanol of the formula,

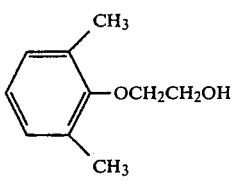

with a carboxylic acid, carboxylic acid anhydride or carboxylic acid halide at a temperature from 0° C. to 100° C. in an inert solvent (e.g., benzene, toluene, xylene, ether, tetrahydrofuran or acetone or a mixture thereof), for 0.5 to 10 hours in the presence of a condensing agent (e.g., triethylamine, pyridine or N,N-diethylaniline).

Procedure B

The 2,6-dimethylphenoxy compound of the formula,

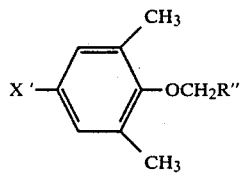

wherein X' is $C_{1-4}$ alkylcarbonyl or benzoyl and R" is $C_{1-4}$ alkoxycarbonyl or $C_{1-6}$ alkylcarboxymethyl, can be prepared by reacting a 2,6-dimethylphenoxyacetic acid alkyl ester of the formula,

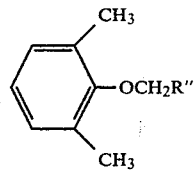

wherein R" is as defined above, with a corresponding carboxylic acid anhydride or carboxylic acid halide at a temperature from 0° C. to 100° C. in an inert solvent (e.g., carbon disulfide or nitromethane) for 0.5 to 10 hours in the presence of a Friedel-crafts catalyst (e.g., aluminium chloride, boron trifluoride, stannic chloride, titanium tetrachloride or zirconium tetrachloride).

Procedure C

The 2,6-dimethylphenoxy compound of the formula,

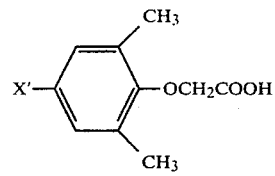

wherein X' is as defined above can be prepared by reacting a 2,6-dimethylphenoxyacetic acid alkyl ester of the formula,

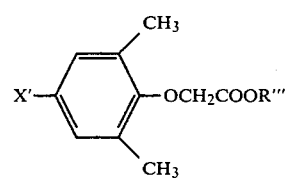

wherein X' is as defined above and R''' is $C_{1-4}$ alkyl, with an alkali or acid catalyst (e.g., sodium hydroxide, potassium hydroxide or sulfuric acid) at a temperature from 0° C. to 100° C. in an aqueous solution for 0.5 to 10 hours.

Procedure D

The 2,6-dimethylphenoxy compound of the formula,

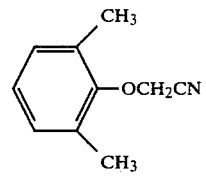

can be prepared by reacting 2,6-dimethylphenoxyacetamide of the formula,

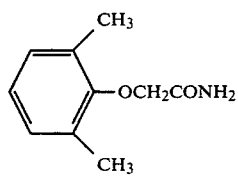

with a dehydrating agent (e.g., $P_2O_5$) at a temperature from 50° C. to 200° C. for 0.5 to 10 hours, or with an alkali (e.g., sodium hydroxide) in a heterogeneous solution at a temperature from 0° C. to 60° C. in the presence of a phase transfer catalyst (e.g., benzyltriethyl ammonium chloride).

The 2,6-dimethylphenoxy compound (I) thus produced may be purified, if necessary, by a conventional procedure such as recrystallization, distillation or column chromatography.

Specific examples of the 2,6-dimethylphenoxy compound (I) thus prepared are shown in Table 1 below:

Table 1

| Procedure | Compound No. | X | R | Physical properties | Formula | Calcd. C | Calcd. H | Calcd. N | Found C | Found H | Found N |
|---|---|---|---|---|---|---|---|---|---|---|---|
| A | (1) | H | —CH$_2$OCCH$_3$ ‖ O | b.p. 103° C./0.65 mmHg | C$_{12}$H$_{16}$O$_3$ | 69.21 | 7.74 | | 69.09 | 7.85 | |
| A | (2) | " | —CH$_2$OCHEt ‖ O | b.p. 108°–110° C./4 mmHg | C$_{13}$H$_{18}$O$_3$ | 70.25 | 8.16 | | 70.41 | 8.03 | |
| A | (3) | " | —CH$_2$OCCH$_2$Cl ‖ O | b.p. 132°–135° C./0.8 mmHg | C$_{12}$H$_{15}$ClO$_3$ | 59.39 | 6.23 | | 59.31 | 6.23 | |
| A | (4) | " | —CH$_2$OCCHCl$_2$ ‖ O | b.p. 130°–131° C./0.25 mmHg | C$_{12}$H$_4$Cl$_2$O$_3$ | 52.01 | 5.09 | | 51.97 | 4.96 | |
| A | (5) | " | —CH$_2$OCCCl$_3$ ‖ O | b.p. 141°–143° C./0.5–0.6 mmHg | C$_{12}$H$_{13}$Cl$_3$O$_3$ | 46.26 | 4.21 | | 46.14 | 4.15 | |
| A | (6) | H | —CH$_2$OC—⟨H⟩ ‖ O | b.p. 147°–149° C./0.5 mmHg | C$_{17}$H$_{24}$O$_3$ | 73.88 | 8.75 | | 73.73 | 8.78 | |
| B | (7) | CH$_3$CO— | —COOCH$_3$ | m.p. 82°–82.5° C. | C$_{13}$H$_{16}$O$_4$ | 66.09 | 6.83 | | 65.91 | 6.82 | |
| C | (8) | CH$_3$CO— | —COOH | m.p. 165°–167° C. | C$_{12}$H$_{14}$O$_4$ | 64.86 | 6.35 | | 64.88 | 6.29 | |
| B | (9) | ⟨⟩—CO | —COOCH$_3$ | m.p. 67.5°–68.5° C. | C$_{18}$H$_{18}$O$_4$ | 72.47 | 6.08 | | 72.34 | 6.06 | |
| B | (10) | CH$_3$CO— | —CH$_2$OCOCH$_3$ | $n_D^{21.6}$ 1.5165 | C$_{14}$H$_{18}$O$_4$ | 67.19 | 7.25 | | 67.44 | 7.15 | |
| D | (11) | H | CN | b.p. 86°–88° C./0.6 mmHg | C$_9$H$_9$NO | 73.45 | 6.16 | 9.52 | 73.21 | 6.13 | 9.31 |

Practical and presently preferred embodiments of the production of 2,6-dimethylphenoxy compound (I) are illustratively shown in the following examples:

EXAMPLE 1 (Procedure A)

To a 500 ml of anhydrous benzene containing 170 g of 2-(2,6-dimethylphenoxy)-ethanol and 134 g of triethylamine was added dropwise with stirring 104 g of acetyl chloride at below 40° C. After completion of the addition, the resulting mixture was continuously stirred for a while, and then heated at 60° C. for 1 hour. The deposited salt was removed by filtration, and the benzene filtrate was washed with water, 5% aqueous sodium hydrogen carbonate solution and water, then dried over anhydrous magnesium sulfate.

After evaporation of the solvent, the oily substance was distilled under reduced pressure to obtain 200 g of a distillate, 2-(2,6-dimethylphenoxy)-ethyl acetate, b.p. 103° C./0.65 mmHg.

EXAMPLE 2 (Procedure B)

7 Grams of methyl 2,6-dimethylphenoxyacetate, 3.4 ml of acetic anhydride and 100 ml of carbon disulfide were mixed at 0° C., and to the mixture was added 17.9 g of aluminum chloride, and the resulting mixture was heated until gas was evolved. After the gas-evolution was ceased, the reaction mixture was refluxed for 30 minutes under heating. Then water was added to the solution. The resulting mixture was extracted with diisopropyl ether, washed with water, dried over anhydrous magnesium sulfate. The oily solution was concentrated to obtain an oily substance. The oily substance was chromatographed on silica gel to obtain 6.1 g of methyl 4-acetyl-2,6-dimethylphenoxyacetate, $n_D^{21.6}$ 1.5165.

EXAMPLE 3 (Procedure C)

To a 10 ml of 10% sodium hydroxide aqueous solution, was added 1.5 g of 2,6-dimethyl-4-acetylphenoxyacetic acid methyl ester with stirring.

After the mixture became homogeneous, the clear solution was acidified with 10% hydrochloric acid aqueous solution. Then the precipitate was filtrated, recrystallized from a solution of methanol and water to obtain 1.1 g of 2,6-dimethyl-4-acetylphenoxy acetic acid, m.p. 165.5°–167° C.

EXAMPLE 4 (Procedure D)

500 Milligrams of benzyltriethyl ammonium chloride and 13.4 g of 2,6-dimethylphenoxyacetamide was added to a heterogeneously mixed solution of 182 ml of chloroform and 60 g of 50% sodium hydroxide aqueous solution, and the solution was stirred vigorously at room temperature for two hours. After completion of reaction, the chloroform phase was separated, and the reaction solution was washed with water, dried over anhydrous magnesium sulfate, and freed from the solvent to obtain an oily substance. The distillation under reduced pressure of the reaction mixture gave 9.7 g of a distillate, 2,6-dimethylphenoxyacetonitrile, b.p. 86°–88° C./0.6 mmHg.

In the actual application as a plant growth regulator, the 2,6-dimethylphenoxy compound (I) may be used alone without incorporation of any other ingredient such as a carrier or a diluent, but for easier application, is used in any of ordinarily adopted forms such as, for example, dusts, wettable powders, oil sprays, aerosols, tablets, emulsifiable concentrates, granules and fine granules. In order to formulate these preparations, the 2,6-dimethylphenoxy compound (I) may be admixed with such solid carriers or diluents as mineral powders (e.g. talc, bentonite, montomorillonite, clay, kaolin, diatomaceous earth, mica, apatite, vermiculite, gypsum, calcium carbonate, pyrophyllite, sericite, pumice, sulfur, active carbon, slaked lime), plant powders (e.g., soybean, wheat, wood, walnut shell, saw dust, bran, bark, plant extract residue, tobacco, starch, crystalline cellulose), polymeric material powders (e.g., petroleum resin, polyvinyl chloride, dammar gum, ketonic resin), fiber products (e.g., paper, corrugated cardboard, old rags), chemical fertilizers (e.g., ammonium sulfate, ammonium phosphate, ammonium nitrate, urea, ammonium chloride), alumina or wax, or with such liquid carriers or diluents as alcohols (e.g., methanol, ethanol, ethylene glycol, benzyl alcohol), aromatic hydrocarbons (e.g., benzene, toluene, xylene, methylnaphthalene), aliphatic hydrocarbons (e.g., kerosene, hexane), chlorinated hydrocarbons (e.g., chloroform, carbon tetrachloride, monochlorobenzene), ethers (e.g., diethyl ether, dioxane, tetrahydrofuran, ethylene glycol ethyl ether), ketones (e.g., acetone, methyl ethyl ketone, cylohexanone), esters (e.g., ethyl acetate, butyl acetate, ethylene glycol acetate), acid amides (e.g., N,N-dimethylformamide), nitriles (e.g., acetonitrile) or sulfoxides (e.g., dimethylsulfoxide). If necessary, other additives such as binding and/or dispersing agent (e.g., gelatin, casein, sodium alginate, CMC, starch, gum arabic powder, lignosulfonate, bentonite, polyoxypropyleneglycol ether, polyvinyl alcohol, pine oil, liquid or solid paraffine), stabilizer (e.g., isopropyl phosphate, tricresyl phosphate, tall oil, epoxidized oil, surfactant, fatty acid, fatty acid ester) or emulsifier (e.g., alkyl sulfonate, polyoxyethylene alkyl sulfate, alkyl arylsulfonate, polyethylene glycol alkyl ether, polyoxyethylene alkyl aryl ether), wetting agent (e.g., dodecyl benzenesulfonate, lauryl sulfate), may be incorporated into the preparations. Further, the preparations may include extending agents as conventionally employed. In addition thereto, they may be used in admixture with such agricultural chemicals as fungicides, insecticides, nematocides and miticides and with fertilizers.

The foregoing preparations generally contain 0.1 to 95.0% by weight, preferably 0.2 to 90.0% by weight of the active ingredient (including other ingredient mixed). A suitable amount of the preparations applied is generally 10 g to 1000 g/10 are, and the concentration of the preparations applied is preferably within the range of 0.001 to 0.1% by weight. Since, however, the amount and concentration depend upon the preparation forms, application times, application methods, application sites and plants, they may be properly increased or decreased irrespective of the aforesaid ranges.

Practical embodiments of the plant growth regulating composition according to the present invention are illustratively shown in the following examples, wherein parts and % are by weight.

Preparation example 1—Dust

2 Parts of the compound (7) and 98 parts of clay were thoroughly pulverized and mixed together to obtain a dust containing 2% of the active ingredient. In application, the dust was dusted as such.

Preparation example 2—Dust

3 Parts of the compound (9) and 97 parts of talc were thoroughly pulverized and mixed together to obtain a dust containing 3% of the active ingredient. In application, the dust was dusted as such.

Preparation example 3—Wettable powder

50 Parts of the compound (1), 2.5 parts of a wetting agent of the dodecylbenzenesulfonate type, 2.5 parts of a dispersing agent of the sodium lignosulfonate type and 45 parts of diatomaceous earth were thoroughly pulverized and mixed together to obtain a wettable powder containing 50% of the active ingredient. In application, the wettable powder was diluted with water, and the resulting solution was sprayed.

Preparation example 4—Emulsifiable concentrate

10 Parts of the compound (1), 40 parts of dimethyl sulfoxide, 40 parts of xylene and 10 parts of an emulsifier of the polyoxyethylene dodecylphenol ether type were mixed together to obtain an emulsifiable concentrate containing 10% of the active ingredient. In application, the emulsifiable concentrate was diluted with water, and the resulting emulsion was sprayed.

Preparation example 5—Granule

5 Parts of the compound (7), 93.5 parts of clay and 1.5 parts of a binder of the polyvinyl alcohol type were thoroughly pulverized and mixed together, kneaded with water and then granulated and dried to obtain a granule containing 5% of the active ingredient. In application, the granule was applied as it is or may be mixed with soil.

Preparation example 6—Floating type granule

10 Parts of the compound (7) was sprayed on 85 parts of pumice having an adjusted particle size of 16 to 32 mesh to allow the compound to soak into the pumice. Thereafter, 5 parts of liquid paraffin was further sprayed thereon to obtain a floating type granule containing 10% of active ingredient. In application, the granule was applied as it is.

Preparation example 7—Coating type granule

10 Parts of the compound (7) was sprayed on 77 parts of silica sand having an adjusted particle size of 16 to 32 mesh, and then 3 parts of a 10% aqueous polyvinyl alcohol solution was further sprayed thereon. The mixture was blended with 10 parts of white carbon to obtain a coating type granule containing 10% of active ingredient. In application, the granule was applied as it is.

Preparation example 8—Granule

10 Parts of the compound (7), 30 parts of bentonite, 1 part of calcium lignosulfonate, 0.1 part of sodium laurylsulfate and 58.9 parts of clay were mixed. The mixture was kneaded with the addition of water, granulated through a screen of 7 mm. in mesh size and dried. Thus, a granule containing 10% of active ingredient was obtained. In application, the granule may be applied as it is or in the form of aqueous dilute solution.

Preparation example 9—Water-surface-spreading oil-based liquid

1 Part of the compound (1), 10 parts of polyoxypropylene glycol monoether and 89 parts of kerosene were mixed to obtain a water-surface-spreading oil-based liquid containing 1% of active ingredient. In application, the liquid was applied as it is.

Some of the test results which show the plant growth regulating effects of the 2,6-dimethylphenoxy compound (I) are shown in the following Test Examples wherein part(s) are by weight. In these Test Examples the numbers of the compounds according to this invention correspond to those as shown in Table 1, while the numbers of the known compounds for comparison correspond to those as shown in the following Table 2.

Table 2

| Compound No. | Chemical structure | Literature |
|---|---|---|
| DMPA | 2,6-dimethylphenyl-OCH$_2$COOCH$_3$ (with CH$_3$ groups at 2,6 positions) | German Offenlegungsschrift 2,407,148; British Pat. No. 1,450,005 |
| B-9 | CH$_2$CONHN(CH$_3$)$_2$ / CH$_2$COOH | U.S. Pat. No. 3,257,414; Japanese Patent publication 14829 (1967) |

Test Example 1

500 Grams of a synthetic soil comprising coastal sand, mountain soil and peat was packed into each of a number of 12 cm unglazed pots. In each pot were cultivated three Pot-mum plants (variety: Snow Ridge). Two weeks after planting, the plants were pinched, and, 2 weeks after pinching (when new buds had formed), the compounds given in Table 3 were applied, in the concentrations also given in the Table, one each to the plants in a respective pot. On the 42nd day after the chemical treatment, the plants were observed to investigate the plant growth-regulating effects of the compounds. The results obtained were as shown in Table 3.

The evaluation of the effects was carried out by determining the increase in height of the plant by measuring the difference between the initial height of the Pot-mum at the time of chemical treatment an the height thereof on the 42nd day after the chemical treatment, and was represented by a growth index calculated by taking as 100 the increase in height of an untreated plant. The value is an average value of three Pot-mum plants.

Table 3

| Compound No. | Pot-mum test Spray treatment (4000 ppm) | Soil treatment | Phytotoxicity Spray | Phytotoxicity Soil |
|---|---|---|---|---|
| (1) | 81 | 49 (25 mg/pot) | — | — |
| (2) | 67 | 68 (20 mg/pot) | — | — |
| (3) | 96 | 58 (20 mg/pot) | — | — |
| (4) | 91 | 54 (20 mg/pot) | — | — |
| (5) | 84 | 70 (20 mg/pot) | — | — |
| (6) | 47 | 52 (20 mg/pot) | — | — |
| (7) | 67 | 38 (50 mg/pot) | — | — |
| (8) | 65 | 42 (50 mg/pot) | — | — |
| (9) | 65 | 57 (50 mg/pot) | — | — |
| (10) | 79 | 51 (20 mg/pot) | — | — |
| (11) | 77 | 47 (20 mg/pot) | — | — |
| DMPA | 54 | 70 (20 mg/pot) | ++ | + |
| " |  | 65 (25 mg/pot) |  | + |
| " |  | 42 (50 mg/pot) |  | +++ |
| B-9 | 85 |  |  | — |
| Control | 100 | 100 | — | — |

≠Note:
The symbols of phytotoxicity mean as follows:
- — : No phytotoxicity.
- + : The leaf became yellow.
- ++ : The leaf became brown and leaf edges were dead.
- +++ : All the leaf portions became markedly brown to be dead.

Test Example 2

500 Grams of soil from a paddy field were packed into each of a number of plastic Neubauer pots (Neubauer is a Trade Mark). To the soil in each respective pot were added 25 mg (50 p.p.m. per part of the soil) of one each of the compounds given in Table 4, together with suitable amount of fertilizer and water. Thereafter, 25 seeds of barley (variety: Yunagi) were sowed to investigate the influence of the chemicals on the initial growth of the barley. The results obtained were as shown in Table 4.

Table 4

| Neubauer pot test | |
|---|---|
| Compound No. | Growth Index |
| (1) | 90 |
| (2) | 78 |
| (3) | 83 |
| (4) | 87 |
| (5) | 80 |
| (6) | 81 |
| (7) | 88 |
| (8) | 85 |
| (9) | 81 |
| (10) | 91 |
| (11) | 91 |
| No treatment | 100 |

What is claimed is:

1. A method for regulating the growth of a plant which comprises applying to the plant a plant growth regulating effective amount of a 2,6-dimethylphenoxy compound of the formula,

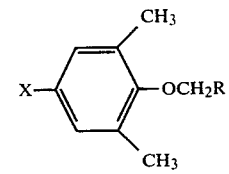

wherein R is hydroxycarbonyl, C$_{1-4}$ alkoxycarbonyl, C$_{1-6}$ alkylcarboxymethyl, mono-, di- or tri-halo C$_{1-4}$ alkylcarboxymethyl or nitrile; X is hydrogen or C$_{1-4}$ alkylcarbonyl, when R is C$_{1-6}$ alkylcarboxymethyl, mono-, di- or tri-halo C$_{1-4}$ alkyl carboxymethyl or nitrile; and X is C$_{1-4}$ alkylcarbonyl or benzoyl, when R is hydroxycarbonyl or C$_{1-4}$ alkoxycarbonyl.

2. The method according to claim 1, wherein X is a hydrogen atom and R is methylcarboxymethyl, ethylcarboxymethyl or cyclohexylcarboxylmethyl group.

3. The method according to claim 1, wherein X is a hydrogen atom and R is a chloromethylcarboxymethyl, chloromethylcarboxymethyl or trichloromethylcarboxymethyl group.

4. The method according to claim 1, wherein X is an acetyl or benzoyl group and R is a methoxycarbonyl group.

5. The method according to claim 1, wherein X is an acetyl group and R is a hydroxylcarbonyl group.

6. The method according to claim 1, wherein X is an acetyl group and R is a methylcarboxymethyl group.

7. The method according to claim 1, wherein X is a hydrogen atom and R is a cyano group.

8. The method according to claim 1, wherein the plant is ornamental plant or fruit tree.

9. A method according to claim 1, wherein the 2,6-dimethylphenoxy compound has the formula

10. A method according to claim 1, wherein the 2,6-dimethylphenoxy compound has the formula
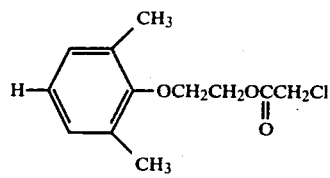
11. A method according to claim 1, wherein the 2,6-dimethylphenoxy compound has the formula
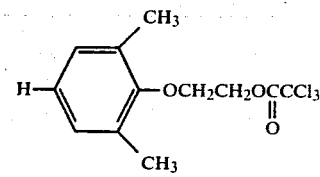
12. A method according to claim 1, wherein the 2,6-dimethylphenoxy compound has the formula
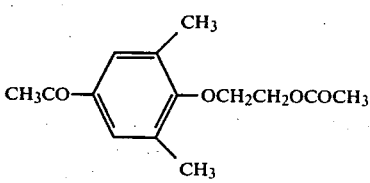
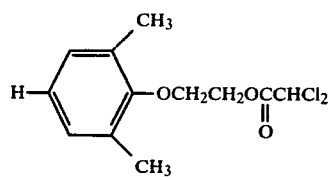
* * * * *